United States Patent [19]

Withers, Jr. et al.

[11] Patent Number: 5,385,105
[45] Date of Patent: Jan. 31, 1995

[54] BURNABLE WASTES COLLECTOR WITH LIQUID ABSORBER AND IDENTIFIER

[75] Inventors: L. Andrew Withers, Jr., Atlanta; David W. Hughes, Chamblee, both of Ga.

[73] Assignee: McDonald, Withers & Hughes, Inc., Atlanta, Ga.

[21] Appl. No.: 247,650

[22] Filed: May 23, 1994

Related U.S. Application Data

[60] Continuation-in-part of Ser. No. 890,022, May 28, 1992, Pat. No. 5,323,719, which is a continuation-in-part of Ser. No. 699,915, May 14, 1991, Pat. No. 5,167,193, and a continuation-in-part of Ser. No. 737,427, Jul. 29, 1991, Pat. No. 5,163,375, which is a continuation-in-part of Ser. No. 26,853, Mar. 5, 1993, which is a division of Ser. No. 757,132, Sep. 10, 1991, Pat. No. 5,259,501.

[51] Int. Cl.$^6$ .............................................. F23G 5/00
[52] U.S. Cl. .................................. 110/346; 110/235; 110/242; 110/237; 110/238; 206/371; 206/365; 206/366; 588/249
[58] Field of Search ............... 588/249; 110/235, 242, 110/346, 237, 238; 206/371, 365, 366

[56] References Cited

U.S. PATENT DOCUMENTS

| | | | |
|---|---|---|---|
| 746,815 | 12/1903 | Ghiradelli | 220/620 |
| 1,368,874 | 2/1921 | Zender . | |
| 1,607,923 | 11/1926 | Sebell | 220/620 |
| 1,643,252 | 9/1927 | McCrery | 220/620 |
| 1,767,583 | 6/1930 | Frick et al. | 221/102 |
| 2,382,932 | 8/1945 | Young | 221/102 |
| 3,072,517 | 1/1963 | Gaylord | 220/620 |
| 3,086,674 | 4/1963 | Scheuerman | 156/83 |
| 3,292,776 | 12/1966 | Penn | 206/43 |

(List continued on next page.)

FOREIGN PATENT DOCUMENTS

| | | | |
|---|---|---|---|
| 989812 | 5/1951 | France | 221/25 |
| 2040268 | 1/1980 | United Kingdom . | |

OTHER PUBLICATIONS

Syd Syringe and Needle Disposers (leaflet), Bemis Health Care (date not available).
Syd Large Volume Diohazard Disposer (leaflet), Bemis Health Care (date not available).
Sharpsafe Bio-Hazardous Waste Containment System (two leaf brochure) by Concord Labatories, Inc. (date not available).
Terminal Keepers for Sharps and Broken Glass (leaflet by Whitney Products, Inc. (date not available).
Sharpsafe Directions for Assembly and Disposal (leaflet) by Concord/Portex, A Smiths Industries Medical Systems Company, Jan. 22, 1990.
Terminal Laboratory Deodorant (leaflet) by Whitney Products, Inc. (date not available).
Terminal Biohazard System for Laboratory, Hospital & Clinic (leaflet) by Whitney Products, Inc. (date not available).
Pages 32, 33 and 47 of Pigalog (catalog) by New Pig Corporation (date not available).
The Microban Effect in Health Care Products Inherent Protection Against Hospital Cross-Contamination (leaflet) by Microban Products co., 1983.
Safe-T-Med, Inc., Advertisement, HPN, Apr. 15, 1993.
Safe-T-Med, Inc., Instruction Sheet.
"Hospital Human Waste Management," Vernacare Corporation, Oakville, Ontario, Canada, ©1990.

*Primary Examiner*—Edward G. Favors
*Attorney, Agent, or Firm*—Hopkins & Thomas

[57] ABSTRACT

The system (10) for collecting and disposing of contaminated waste products such as medical sharps and other medical wastes includes a housing (11) and its telescopic cover (9) which are fabricated of biodegradable and combustible material such as natural cellulose and non-natural cellulose. An absorbent biodegradable and combustible absorption package (30) or insert (35) can be placed in the bottom of the holding chamber (12) for absorbing any liquids emitted from the sharps and other wastes, and for enhancing the combustion of the medical sharps and other wastes when the housing is placed in a furnace. When the housing is burned it evolves no more than trace levels of sulfur or chlorine and yields substantially only biodegradable ash.

34 Claims, 5 Drawing Sheets

U.S. PATENT DOCUMENTS

| | | | |
|---|---|---|---|
| 5,039,004 | 8/1991 | Simpson | 229/132 |
| 5,040,972 | 8/1991 | Kleinhenz et al. | 432/72 |
| 5,065,939 | 11/1991 | Boothe et al. | 229/151 |
| 5,086,716 | 2/1992 | Lafser, Jr. | 110/345 |
| 5,096,114 | 3/1992 | Higginbotham | 229/117.15 |
| 5,107,990 | 4/1992 | Wicherski et al. | 206/366 |
| 5,152,394 | 10/1992 | Hughes | 206/366 |
| 5,163,375 | 11/1992 | Withers et al. | 110/346 |
| 5,167,193 | 12/1992 | Withers et al. | 110/346 |
| 5,235,795 | 8/1993 | DeBusk | 53/467 |
| 5,245,117 | 9/1993 | Withers et al. | 588/249 |
| 3,503,080 | 3/1970 | Laufer et al. | 4/112 |
| 3,543,996 | 12/1970 | West | 220/24 |
| 3,599,249 | 8/1971 | Reed | 4/112 |
| 3,637,072 | 1/1972 | Narusawa et al. | 229/43 |
| 3,746,240 | 7/1973 | Flynn | 229/14 |
| 3,858,722 | 1/1975 | Haas | 206/380 |
| 3,962,732 | 6/1976 | Mills | 4/112 |
| 4,011,606 | 3/1977 | Scrafield et al. | 4/112 |
| 4,023,216 | 5/1977 | Li | 4/110 |
| 4,136,798 | 1/1979 | Oberstein | 220/408 |
| 4,182,478 | 1/1980 | Etes | 229/62 |
| 4,250,998 | 2/1981 | Taylor | 206/570 |
| 4,254,862 | 3/1981 | Barratt | 206/63.3 |
| 4,321,999 | 3/1982 | Higgins | 206/370 |
| 4,328,904 | 5/1982 | Iverson | 220/256 |
| 4,351,434 | 9/1982 | Elisha | 206/366 |
| 4,375,849 | 3/1983 | Hanifl | 206/366 |
| 4,410,086 | 10/1983 | Simpson | 206/366 |
| 4,452,358 | 6/1984 | Simpson | 206/366 |
| 4,454,944 | 6/1984 | Shillington et al. | 206/366 |
| 4,485,918 | 12/1984 | Mayer | 206/366 |
| 4,488,643 | 12/1984 | Pepper | 206/366 |
| 4,494,652 | 1/1985 | Nelson | 206/366 |
| 4,520,926 | 6/1985 | Nelson | 206/366 |
| 4,657,138 | 4/1987 | Watson | 206/366 |
| 4,674,676 | 6/1987 | Sandel et al. | 229/142 |
| 4,715,498 | 12/1987 | Hanifl | 206/366 |
| 4,722,472 | 2/1988 | Bruno | 229/128 |
| 4,736,844 | 4/1988 | Scott et al. | 206/370 |
| 4,738,362 | 4/1988 | Burns et al. | 206/366 |
| 4,767,008 | 8/1988 | Warnecke et al. | 206/570 |
| 4,779,728 | 10/1988 | Hanifl et al. | 206/366 |
| 4,804,090 | 2/1989 | Schuh et al. | 206/366 |
| 4,807,752 | 2/1989 | Chodorow | 206/63.5 |
| 4,808,286 | 2/1989 | Angelo, II | 204/157.15 |
| 4,816,307 | 3/1989 | Honeycutt | 428/34.1 |
| 4,828,107 | 5/1989 | Spencer | 206/366 |
| 4,842,138 | 6/1989 | Sandel et al. | 206/370 |
| 4,848,570 | 7/1989 | Gosciniak | 206/366 |
| 4,848,587 | 7/1989 | Nipp | 206/571 |
| 4,850,290 | 7/1989 | Benoit et al. | 110/346 |
| 4,874,103 | 10/1989 | Quisenberry et al. | 220/1 T |
| 4,900,500 | 2/1990 | Honeycutt | 264/263 |
| 4,908,882 | 3/1990 | Williams et al. | 4/261 |
| 4,919,264 | 4/1990 | Shinall | 206/210 |
| 4,927,076 | 5/1990 | Simpson | 229/132 |
| 4,936,449 | 6/1990 | Conard et al. | 206/366 |
| 4,940,157 | 7/1990 | Inagaki | 220/254 |
| 4,969,554 | 11/1990 | Sawaya | 206/370 |
| 4,972,950 | 11/1990 | Shillington | 206/366 |
| 4,973,315 | 11/1990 | Sincock | 604/192 |
| 4,979,683 | 12/1990 | Busdeker | 241/36 |
| 4,982,843 | 1/1991 | Jones | 206/366 |
| 4,984,686 | 1/1991 | Shillington | 206/366 |
| 4,995,122 | 2/1991 | Mohnhaupt | 4/483 |
| 5,020,665 | 6/1991 | Bruno | 206/366 |
| 5,024,326 | 6/1991 | Sandel et al. | 206/366 |
| 5,033,130 | 7/1991 | Dehaese | 4/452 |
| 5,038,929 | 8/1991 | Kubofcik | 206/210 |

BURNABLE WASTES COLLECTOR WITH LIQUID ABSORBER AND IDENTIFIER

CROSS REFERENCE

This is a continuation-in-part of application Ser. No. 07/890,022 filed May 28, 1992, U.S. Pat. No. 5,323,719, which is a continuation-in-part of application Ser. No. 07/699,915 filed May 14, 1991, U.S. Pat. No. 5,167,193, and application Ser. No. 07/737,427 filed Jul. 29, 1991, U.S. Pat. No. 5,163,375; and this application is a continuation-in-part of application Ser. No. 08/026,853 filed Mar. 5, 1993, which is a division of application Ser. No. 07/757,132 filed Sept. 10, 1991, U.S. Pat. No. 5,259,501.

FIELD OF THE INVENTION

The present invention relates in general to a system for disposing of contaminated medical wastes. More particularly, the invention relates to a collector for collecting and disposing of medical sharps such as hypodermic needle syringes and other medical wastes in a home or health care environment, by collecting the wastes in a housing, transporting the housing to an incinerator and burning tile housing and its contents in the incinerator.

BACKGROUND OF THE INVENTION

The term "medical sharps" generally is defined as medical instruments having a sharp cutting edge or a Sharp point. In the medical environment, sharps comprise hypodermic needle syringes, scalpel blades, and the like. After use, medical sharps are considered contaminated wastes and must be disposed of. Other contaminated medical wastes, including chemo-therapy, pathological and dental wastes, comprise surgical tubing, washcloths, surgical gloves, masks, garments, drapes, cultures of infectious agents, and the like. Additionally, other types of wastes include surgical "kit packs" for performing specific surgical procedures, whereby after use in an operation, such kit packs are considered contaminated wastes. After use, medical sharps and other contaminated medical wastes must be safely collected and disposed of without creating a hazard for the hospital personnel, patients, or visitors of a medical care facility, or for members of the family when used in the home.

Typically in the home environment, medical wastes such as expired medication, medical gauze, and medical tape are discarded in a regular household trash can. However, in situations where the patient receives medical injections away from the medical care facility, such as a diabetic patient who must monitor his or her blood sugar level and then administer self-injections of insulin, the used insulin needle syringes must be safely disposed of so as to avoid presenting a hazard to other members of the family or community. Also, other diseases and medical procedures require the frequent use of needle syringes in the home. Presently, none of the known prior art discloses a collector or receptor for safely discarding contaminated or hazardous medical wastes such as insulin syringes of a diabetic patient in a home environment.

When medical sharps or surgical "kit packs" are being used in a hospital, typically the hospital protocol is to use and immediately dispose of these medical wastes in receptacles, such as in plastic, wall-mounted receptacles or in large receptors placed on the floor having an open top, otherwise known as "kick buckets". Typically the medical waste receptacles are placed in strategic locations throughout the hospital or other medical treatment facility, such as in the patient's rooms, in the hall outside the patient's room, in treatment rooms, operating rooms, and emergency rooms, so as to be available for receiving the medical wastes immediately and conveniently after use by the nurse, physician, or other medical personnel. Additionally, the kick buckets are generally placed in operating rooms and emergency rooms for receiving large volumes of various types of medical wastes. The receptacles must be suitably sized and shaped to receive the anticipated amount of medical waste over a period of time, depending on the protocol of the medical facility, and the receptacles must easily receive yet securely and safely retain the medical waste so as to avoid presenting a hazard to children or to disoriented patients or to curious visitors.

After these receptacles are filled with medical wastes, they are collected for disposal, usually for burning in an incinerator. The collection procedure usually requires housekeeping personnel to move about the hospital with a plastic bag or other relatively large container and to place the filled receptacles in the bag, and to replace the used receptacles with new empty receptacles, for example by dismounting the used plastic receptacles from their wall brackets and mounting the new receptacles in the wall brackets. After replacement and collection of the medical waste receptacles, the collected receptacles are securely packaged in a larger container such as a plastic bag or cardboard box and the bag or box is transported to a burn facility.

During the containment and collection procedure of medical wastes, there is the hazard that the medical waste materials will contaminate the personnel who are handling or are exposed to the wastes. Experience demonstrates that accidents caused by the medical waste materials through skin scratch or puncture and other exposure are occasional causes of injury to personnel and such accidents are a considerable expense to hospitals and insurance companies.

For example, when the used receptacles that are filled with medical wastes are being removed from their holders or being transported, the needle of a syringe can protrude from or escape from its individual receptacle and scratch or puncture the personnel handling the receptacle.

Therefore, it is highly desirable that the use-and-dispose method provides for safe containment and collection of the medical sharps and other wastes within the home and the hospital environment by providing a collector which is puncture resistant and leak resistant.

Another problem can be created during disposal of the medical wastes. The usual method of disposal is incineration, whereby the medical wastes are converted into ash for delivery to a landfill, etc. The disposal systems for the medical wastes range from on-site incinerators to contract disposal services which transport the medical wastes to off-site burn facilities. Generally, the treatment plants incinerate the collectors and the medical wastes contained in the collectors and then bury the residue of the burned medical wastes and collectors in a landfill.

An incineration technique is especially advantageous for disintegrating contaminated sharps and other pathological wastes, because incineration has the ability to convert the contaminated substances into a non-contaminated ash. However, when certain materials such as plastics of a syringe are burned, ashes from the incineration of these materials can become a partially pyrolized plastic residue, which is essentially a tar ash or residue which when buried in a landfill, is non-biodegradable waste. Although the ashes of plastic syringes and some other types of plastic wastes will be delivered to landfills, it is highly desirable to avoid the use of plastic collectors for these wastes, because when plastic collectors are burned they can emit toxic gases to the atmosphere and create even more non-biodegradable ash, which is an undesirable additive to a landfill.

Thus, it would be advantageous to provide a disposable collector system for collecting and disposing of medical sharps and other medical wastes which is safe and efficient to use, which can be specifically constructed in a small size for home use by a diabetic, or which can be constructed in larger sizes for use in the offices of physicians and medical care facilities, and which can be incinerated without the evolution of substantial toxic gases emitted from the collector and which when burned aids in rendering the wastes.

It also would be desirable to fabricate the collector of a combustible material that yields substantially only biodegradable ash upon incineration and to adjust the mass of the collector with respect to the anticipated mass of the wastes to be collected in the collector so as to control the worst case ratio of plastic, nonbiodegradable ash to cellulosic, biodegradable ash.

Further, it would be desirable that contaminated medical wastes be accounted for when being burned, so that the person or medical care facility that generated the waste material receives confirmation that the wastes were delivered to the waste incineration site for proper disposal.

SUMMARY OF THE INVENTION

Briefly described, the present invention comprises a system for collecting and disposing of medical sharps and other medical wastes, which provides a leak resistant, combustible, and biodegradable housing including a closed lower portion and an upper portion with an opening for receiving medical wastes. In one embodiment of the invention the upper portion of the housing includes a lid with an openable area, such as a scored portion of the housing for yieldably opening the upper portion of the housing while normally maintaining the housing closed. A wall bracket is provided for mounting the housing to a wall of a building for releasably holding the housing in a firm and safe condition.

Preferably, the collector housing is formed of a renewable resource or non petroleum-based material, which when incinerated will yield substantially only a biodegradable ash, otherwise known as mineral ash. In a preferred embodiment of the invention, the entire housing is fabricated of material possessing combustible and biodegradable characteristics. When incinerated in a furnace environment the collector initially retains its medical wastes and the heat of combustion of the collector adds to the heat used to render the medical wastes in the collector housing.

One embodiment of the invention is specifically sized and shaped to receive an anticipated amount of insulin syringes in the home environment of a diabetic patient. Additionally, an embodiment has the option of being attached if desired, such as by adhesives, to horizontal or other selected surfaces of different rooms throughout the home so as to be conveniently located for disposal of the used syringes after each self injection of insulin. This embodiment also provides a designated place to collect and dispose of the used insulin syringes in the home environment.

In another embodiment of the invention, a wall-mounted head or lid releasably supports the disposable collector housing, and the wall mounted lid of the housing receives and passes the medical wastes into its collector housing. This head is formed of a clear material such as glass or any other material with glass-like qualities wherein the user can view inside the housing as the medical wastes are collected and fill up the housing. Additionally, the head is cleanable and non-stainable.

Another embodiment of the present invention provides an absorbent material located inside the collector housing for absorbing fluid emitted from or residual on the discarded medical wastes. The absorbent material can comprise a super absorbent formed of sodium acrylate, which is supplied in an amount proportional to the interior dimensions of the collector housing so as to absorb the greatest anticipated amount of liquid to be released in the housing. A preferred form of the absorbent material possesses all or a combination of absorbent, cellulosic, antimicrobial, antibacterial, antifungal, biodegradable, and combustible properties, whereby any residual fluid inside the collector housing tends to be preferentially absorbed and dispersed in the absorbent material to prevent the liquid wastes from spilling from the opening of the container and to protect personnel from coming into direct contact with the liquid medical wastes.

In another embodiment of this invention, the housing comprises a dual-wall construction, wherein the material of the housing also is fabricated of a combustible and biodegradable material. In addition, this embodiment provides an effective approach to controlling the wall thickness of the housing, which substantially increases the puncture-resistance factor of the housing. The dual-wall construction can be combined with an absorptive package or insert within the housing to further improve the leak resistance of the system for collecting and disposing of medical wastes.

Indicia are applied to the exterior of the housing which identifies the housing as containing hazardous waste and which provides a combination of letters and numbers that can be used to identify the particular waste, the origin of the container and its waste, the location of the container and its waste when en route to a waste disposal site, and to confirm that the container and its waste have reached the disposal site and have been burned or otherwise disposed of.

Further, the identifying indicia, which can be applied directly to the collector housing or to a larger transport container that carries several such collector housings, can be used to identify the type of, the origin of, or the specific contents of the collector housing so that the collector housing can be incinerated without having to open the collector housing and so that the collector housing can be incinerated in a manner compatible with the contents of the collector housing.

It is therefore an object of the present invention to provide an apparatus which collects, contains, ships, and disposes of medical wastes in a safe, convenient, and inexpensive manner.

Another object of the present invention is to provide a collector housing which can be suitably sized, shaped, and placed to receive an anticipated amount of insulin syringes in the home environment of a diabetic and which can be delivered to a disposal site and incinerated without removal of the wastes from the housing.

It is yet another object of the present invention to provide a collector housing which is combustible and biodegradable and formed from a renewable resource, otherwise known as a non-petroleum-based material.

A further object of the present invention is to provide a system for collecting and disposing of medical sharps, whereby the housing itself is puncture resistant, leak resistant, rigid, and combustible for safe containment and effective treatment of medical sharps.

It is yet another object of the present invention to provide a collector housing for collecting and disposing of medical wastes in a safe and economical manner, and to provide within the housing an absorptive, antimicrobial, antifungal, antibacterial material whereby when wastes are deposited into the housing, any fluid emitted from the wastes will be absorbed and disinfected.

A further object of this invention is to provide a collector housing for collecting and disposing of medical wastes wherein an absorbent material is contained within the housing adjacent the medical wastes for absorbing liquid emitted from the wastes, Another object of this invention is to provide a system for collecting and disposing of medical wastes, such as syringes used for injecting medication, whereby the system comprises a combustible housing that, upon combustion, fully renders the medical waste within the environment of a furnace.

It is another object of the present invention to provide such a system of collecting and incinerating of medical wastes wherein a combustible housing for collecting the medical wastes is of appropriate mass and rigidity during initial burning to substantially retain the medical wastes therein, until the wastes combust and begin to be reduced to ash.

Another object of the invention is to provide a system for disposing of medical wastes, particularly hypodermic needle syringes and other medical sharps, wherein the wastes are safely contained in a housing, the housing is transported to a burn site and the housing and its contents are burned without opening the housing, and the contents and origin of the housing are identified by external markings on the housing.

A further object of the present invention is to provide a system for collecting and disposing of medical wastes wherein the entire housing is fabricated of a clean burning combustible material that, upon combustion, emits gases which are substantially free of sulfur or chlorine.

A more complete understanding of the present invention will be had by those skilled in the art, as well as an appreciation of additional advantages, which will become apparent upon reading the detailed description of the preferred embodiment and examining the drawings, the the following of which is a brief description.

DETAILED DESCRIPTION

Figures 1, 2:
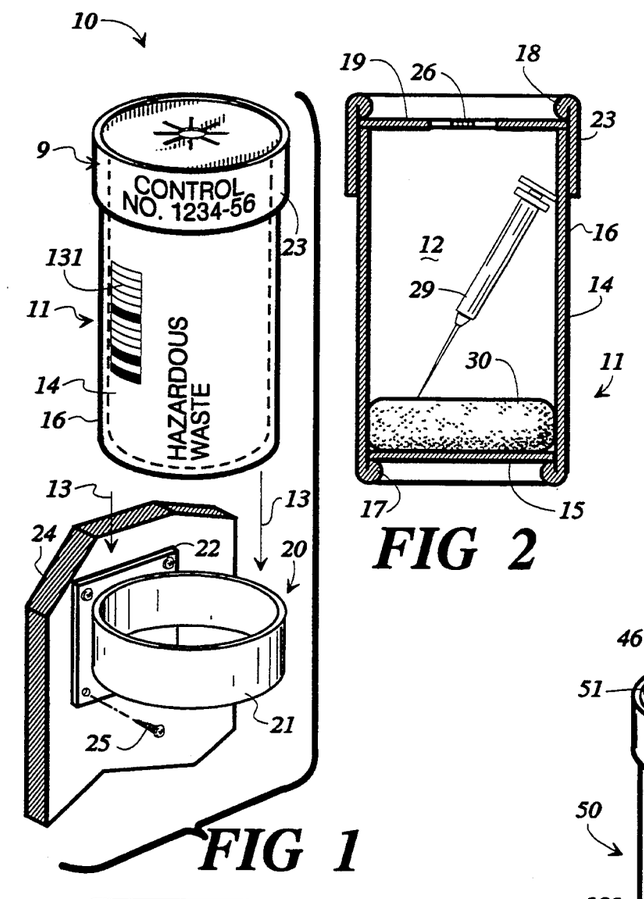
FIG. 1 is a perspective view of the system for collecting and disposing of medical wastes and its wall holder, showing how the housing of the system fits into the wall bracket.
FIG. 2 is a side cross-sectional view of the system for collecting and disposing of medical wastes of FIG. 1, showing a syringe that has been deposited in the collector housing.
Figure 3:
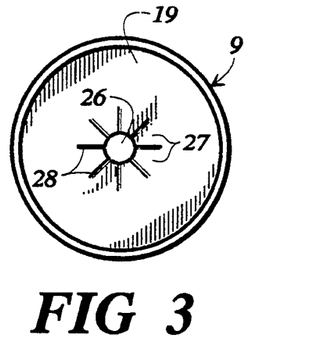
FIG. 3 is a top view of the circular lid of the system for collecting and disposing of medical wastes of FIG. 1.

Referring now in more detail to the drawings, in which like numerals indicate like parts throughout the several views, FIGS. 1-3 illustrate the system 10 for collecting and disposing of medical wastes which includes a cylindrical housing 11 and its wall mount 20, according to the present invention. The housing 11 is shown separated from a wall mount 20 and ready for insertion into a circular sleeve 21 of the wall mount 20 as indicated by the downward directional arrows 13. The wall mount 20 comprises a mounting bracket 22, preferably attached to a wall 24 by multiple screws 25 which extend through openings of the bracket into the wall of the building structure, and the mounting bracket 22 supports the circular sleeve 21 in an upright attitude.

The housing 11 comprises an upper telescoping cover 9 and a lower cylindrical body 14. The upper telescopic cover can be attached, such as by adhesive connection or by helical threads, to the cylindrical body of the housing which includes a cylindrical side wall 16 with the lower end portion of the side wall turned inwardly to form a circular flange or seat 17 (FIG. 2) and the bottom wall or "plug" 15 is positioned inside the side wall and is supported on the seat 17. Lower cylindrical body 14 and its bottom wall 15 define a holding chamber 12 which is open at its upper end. An absorptive insert in the form of an absorption pack 30 resting on bottom wall 15 acts to absorb and disperse liquids throughout the absorption pack and also can be partially penetrated by syringe needles and other medical sharps. The configuration and density of the material of the absorptive insert are selected to absorb the anticipated types and amounts of liquids emitted from the syringes and other items to be placed in the housing 11. The absorptive material of the insert preferably is more absorptive than the material of the housing 11. Usually, a super absorbent material such as sodium acrylate is used as the absorbent material.

The telescoping cover 9 includes a cylindrical side wall 23 which is of sufficient internal breadth to telescopically fit over the upper end of the cylindrical side wall 16 of the lower cylindrical body 14 with a tight fit, and the telescoping cover 9 is of a diameter larger than the space defined by the sleeve 21 of the mounting bracket 22 so that when the housing 11 is moved down into the circular sleeve 21 of the wall mount 20 the cover 9 supports the cylindrical housing 11 in the mounting bracket. The telescoping cover 9 has on its uppermost portion, upper inwardly projecting circular seat 18 and a top wall or "plug" 19 defining a circular aperture 26, with score lines 28 radiating outwardly from the aperture which can separate when medical sharps or other medical wastes are thrust downwardly through the top wall.

The preferred embodiment of the cylindrical housing used for collecting and disposing of medical sharps and other medical wastes is formed of a leak resistant, rigid, combustible material selected from: cellulosic materials, such as paper stock, cardboard, wood, and particle board, non-natural cellulosic materials such as rayon, cellophane, and cellulose-nitrate, and other biodegradable materials such as natural rubber and natural wax, whereby when burned form gases of combustion which yield no more than trace levels of sulfur or chlorine. The cylindrical housing also can be colored by color agents for designating medical sharps, medical wastes, or chemotherapy waste, whereby the coloring agents are also biodegradable. The housing material can include an anti-microbial additive such as a commercially available disinfectant. In addition, it is understood that a cylindrical housing as illustrated in the drawings is only one of many configurations the system for collecting and disposing of medical wastes can take. The housing can be of various sizes and proportions and can be of shapes such as rectangular, octagonal, etc.

FIG. 2 shows a used syringe 29 inserted through the aperture 26 of the telescopic cover 9 and into the holding chamber 12 of the housing 11. The aperture 26 formed in the top wall 19 is sized in accordance with the expected size of the medical waste items to be collected so that the medical sharp or other medical waste must slightly stretch the aperture along the score lines 28 when being inserted in the collector. This tight and yielding fit of the syringe avoids inadvertent escape of a syringe from the collector.

The needles of the syringes which are likely to hold liquid contaminants may penetrate or be in physical proximity to an insert or absorption package 30 at the bottom of the holding chamber 12. The absorption package can be formed of a super absorbent material such as sodium acrylate, or of a group of materials selected from: natural cellulosic, non-natural cellulosic, and other materials which are biodegradable and combustible, with antimicrobial additives, such as commercially available disinfectants. As shown in FIG. 2, this absorption package is placed in the lower portion of the cylindrical housing 11 abutting the bottom plug 15 and the cylindrical side wall 16. In a preferred embodiment, the absorption pack 30 is larger than the effective size of the opening 26 in the top wall and cannot pass through the opening. When the housing 11 is in its upright position with the opening 26 facing upwardly, the absorption pack 30 rests on the bottom of the holding chamber where it is most likely to be engaged by the medical wastes and the liquids emitted therefrom. Should the housing be turned on its side, the absorption pack is influenced by gravity to move toward the lower most area of the holding chamber where the absorption pack is most likely to be engaged by liquids emitted from the syringes or other medical wastes.

Figure 4:
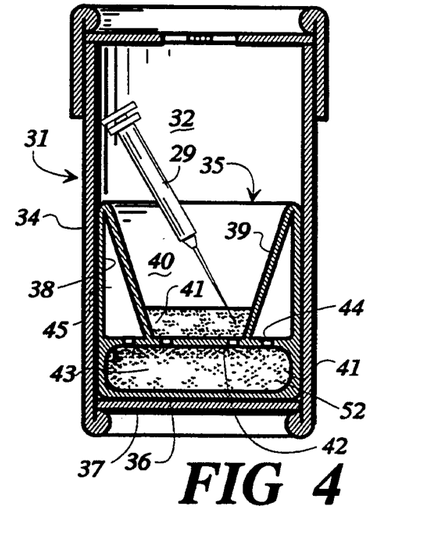
FIG. 4 is a side cross-sectional view of another embodiment and its insert.

FIG. 4 illustrates an additional embodiment of the absorption package of the invention, showing a housing 31 for collecting and disposing of medical sharps and with the absorption package comprising a self-supporting insert 35. The insert fits snugly into the lower portion of the holding chamber 32 of the cylindrical body 34 with a bottom wall 36 of the insert 35 abutting the bottom wall 37 of the housing. The self-supporting insert 35 has an annular outer vertical side wall 38 extending from the bottom wall 36 of the insert, upwards to a height less than or equal to the height of the cylindrical side wall 34. An inwardly and downwardly inclined conically shaped inner wall 39 extends downwardly from the upper edge of the vertical side wall 38 of the insert and intersects horizontal false bottom wall 42 to form a conically shaped receptacle 40, and an annular hollow cavity 45 surrounds the conically shaped receptacle. A cork 41 or other means for being partially penetrated by, and therefore, retaining medical sharps is positioned in the lower portion of the conically shaped receptacle 40. False bottom wall 42 forms lower chamber 43 above bottom wall 36, and absorptive and combustible material 52 is contained in the lower chamber. Thus, the conically shaped receptacle 40 tends to guide the medical wastes inwardly and downwardly toward the cork, etc. 41 in the lower portion of the conically shaped receptacle as the medical sharps and other medical wastes fall downwardly into the receptacle, whereby excess fluids of the wastes will be absorbed by and dispersed in the absorptive and combustible material 52. Multiple air holes 44 are defined in the false bottom wall 42, wherein any excess fluids can have access to the absorption material 52 in the lower chamber 43 to further absorb any fluids emitted from the medical sharps. The air holes 44 also serve as ventilators to enhance combustion within the holding chamber 32, when incinerated.

An additional embodiment of the absorption package or insert comprises free, flowable particulate material which conforms to the shape of the lower portion of the holding chamber when dispersed within the container (not shown).

Figure 5:
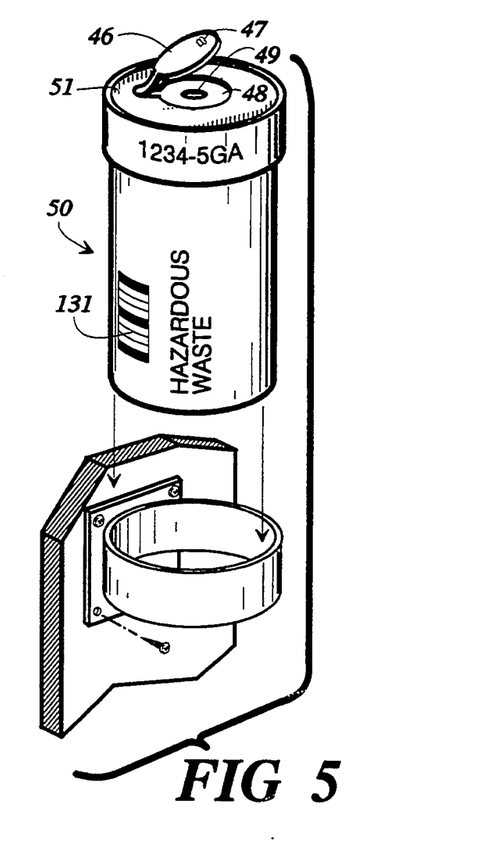
FIG. 5 is a perspective view similar to FIG. 1, but of another embodiment of the invention having a modified lid structure and a wall mounted holder.

FIG. 5 illustrates an additional embodiment 50 of a receptor for medical sharps, wherein the aperture 49 of the top wall 51 is closed by a lid 46 having a tab 47 that can be grasped and pulled upwardly to reveal an inner recessed lip 48 about the aperture 49 for receiving medical waste.

Figure 6:
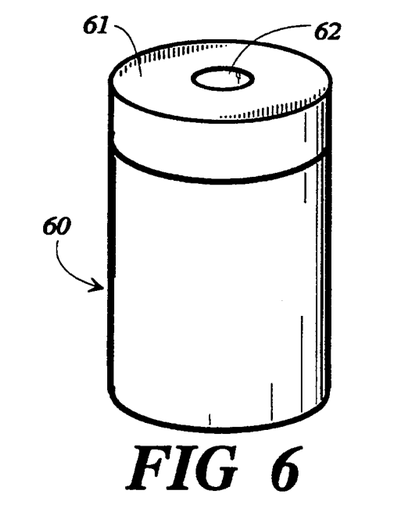
FIG. 6 is a perspective view of a third embodiment of the invention which is of a molded construction.
Figure 7:
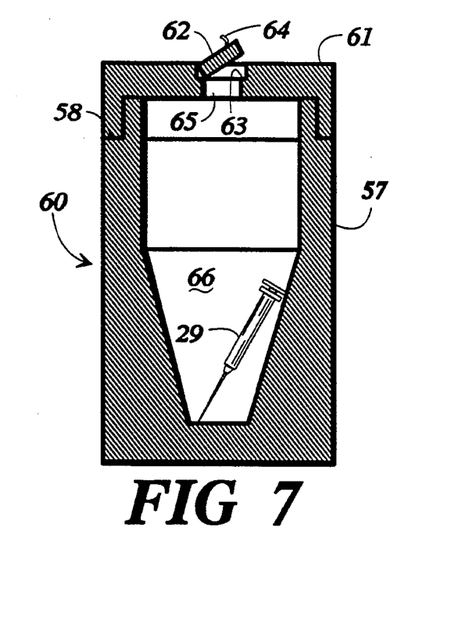
FIG. 7 is a side cross-sectional view of the embodiment of FIG. 6.

FIGS. 6 and 7 illustrate another embodiment of the cylindrical housing 60 which includes a molded monolithic lower housing 57 and a molded top wall or a telescoping cover 61. The cover or top wall 61 defines an aperture 65 and a circular lid 62 which closes the aperture, with the lid 62 having a tab 64 for opening the circular lid. The circular lid 62 abuts an inner recessed flange 63 about the aperture 65.

The housing 60, which can be cylindrical on the outside as shown or other shapes, defines a holding chamber 66 for receiving medical wastes. The inside surfaces can be tapered for funneling the medical sharps 29 and other medical wastes toward a centrally located position, if desired. The lower housing 57 has a recessed annular flange or rim 58 in the upper portion of its annular side wall for receiving the interlocking telescopic cover 61 and the telescopic cover 61 and lower housing 57 form a smooth exterior side wall of the housing 60.

Figure 8:
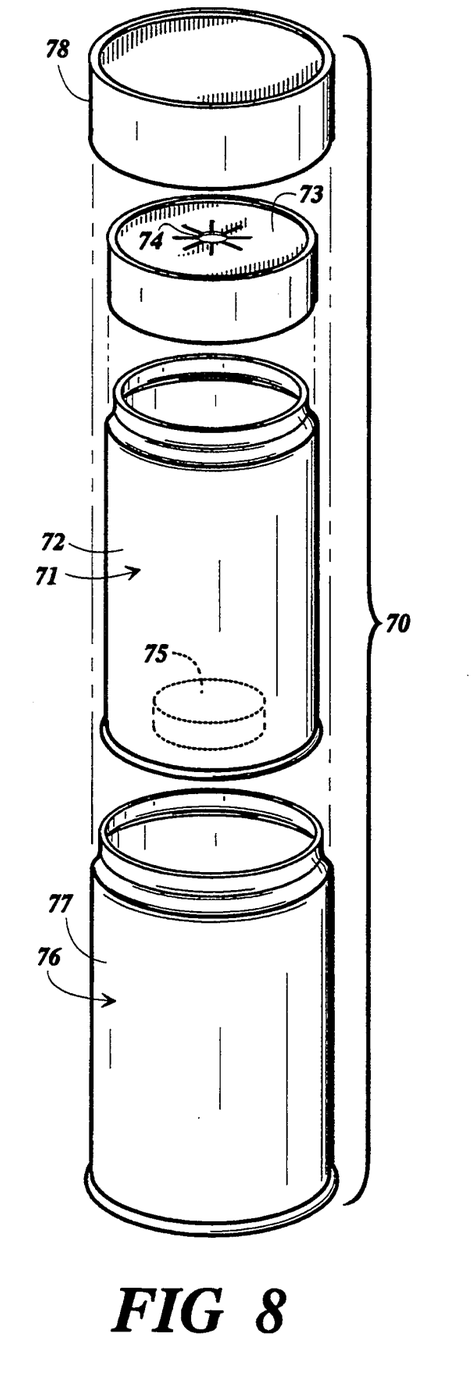
FIG. 8 is an expanded perspective illustration of a dual wall collector.
Figures 9, 10, 11:
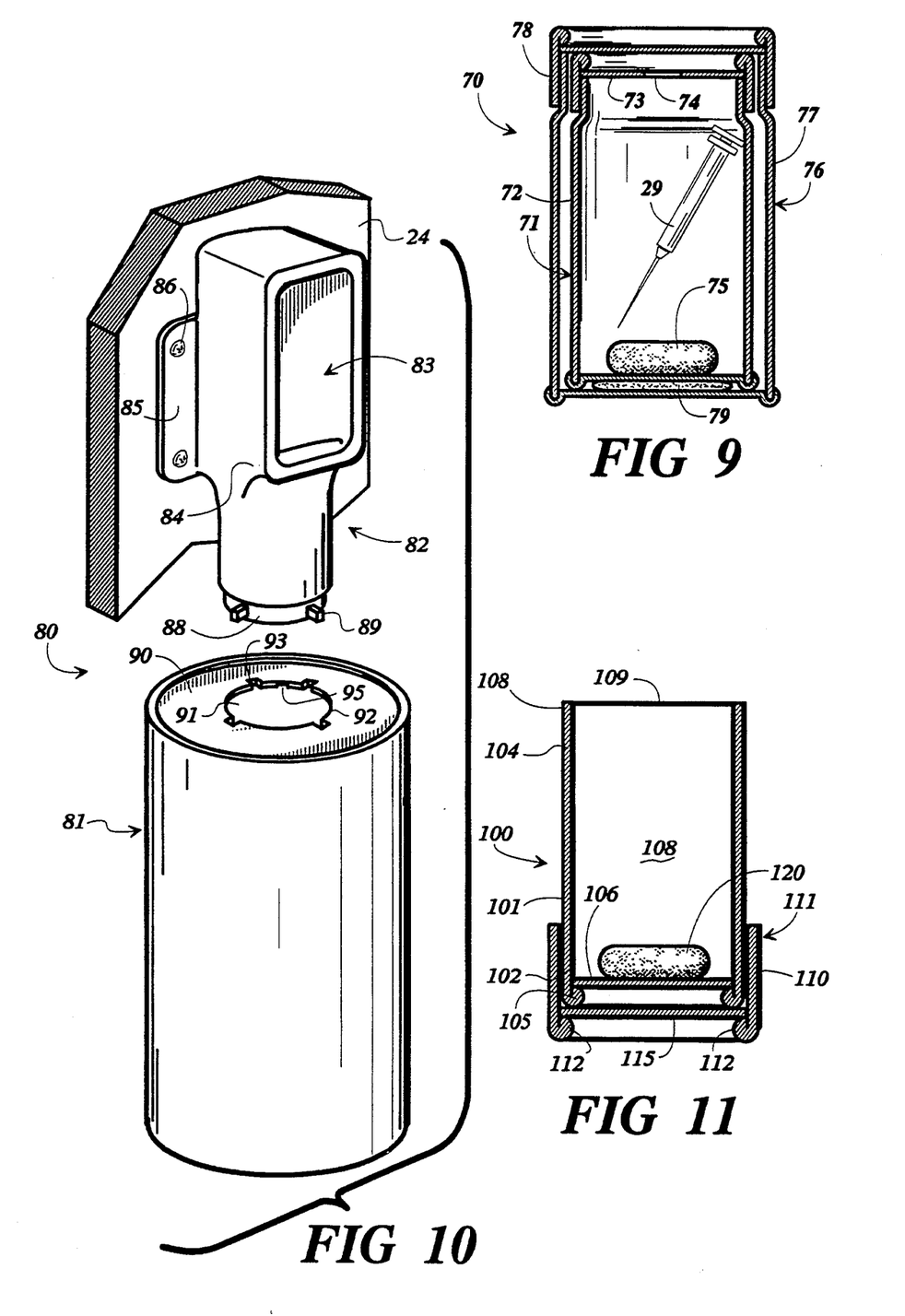
FIG. 9 is a cross sectional illustration of the assembled dual wall collector of FIG. 8.
FIG. 10 is an expanded perspective view of yet another embodiment which includes a lid having a vertically oriented opening and a collector housing, with the housing supported by a wall-mounted head.
FIG. 11 is a side cross-sectional view of another embodiment of the system for collecting and disposing of medical wastes, with the cover mounted on the bottom, leaving the collector open at its top.

FIGS. 8 and 9 illustrate another embodiment 70 of the housing which includes a dual cylindrical side wall structure. This embodiment includes an inner, smaller cylindrical container 71 having a cylindrical body 72, lid 73 with opening 74 formed therein, and an absorption pack 75. The inner container 71 is received in an outer container 76 which includes a cylindrical portion 77 and a lid 78. Typically, the outer lid 78 does not include an opening 74. An additional absorptive pack 79 can be used in the dual wall structure, if desired. The additional absorptive pack 79 is placed outside the inner container, away from the holding chamber of the syringes 29, but inside the exterior container 76. Preferably, the additional absorptive pack 79 is placed at the bottom of the exterior container 76 where it is most likely to be contacted by liquid emitted from the inner container 71.

As illustrated in FIG. 9, where the inner and outer cylindrical containers 71 and 76 are assembled, it can be seen that a dual side wall structure is formed, with the layered side walls presenting additional puncture resistance to the hypodermic needles of the syringes. Further, the dual side walls provide additional structural rigidity to the assembly, so that should the outer cylindrical side wall structure be scarred, punctured, dented or otherwise damaged during shipment or other handling, the inner side wall structure is less likely to be damaged or penetrated, and therefore less likely to have its contents escape from the holding chamber.

FIG. 10 shows another embodiment 80 of the system, having a head 82 mounted to the wall 24. The head 82 defines an elongated opening 83 and a curved chute 84 extending inwardly and downwardly from the opening toward the cylindrical housing 81 below, which receives the medical sharps. The head 82 has a flange 85 with screws 86 or other fasteners for securing the flange to a wall 24. The lower portion of the head 82 defines a cylindrical collar 88 with multiple protruding studs 89 extending outwardly therefrom for releasably locking together the head 82 and the cylindrical housing 81.

The cylindrical housing 81 includes a top wall 90 having an aperture 91. A rim 92 defines the aperture 91 and has open slots 93 formed therein for receiving the studs 89 of the collar 88 of the head 82 to pass through the top wall, and closed notches 95 to nonrotatably mount the housing on the head 82. Therefore, as medical personnel fill the cylindrical housing, they can see through the transparent or translucent head 82 and downwardly through the opening 83 to determine the volume of medical waste present in the housing 81 and replace the housing as necessary.

Figure 12:
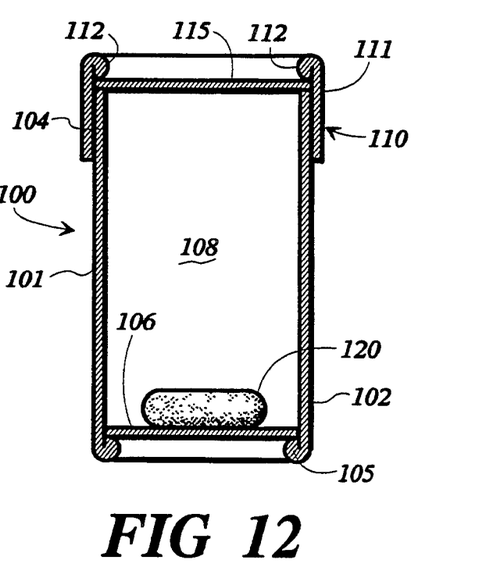
FIG. 12 is a side cross-sectional view of the embodiment of FIG. 11, with the cover closing the top opening.

FIGS. 11 and 12 illustrate an additional embodiment 100 of the system for collecting and disposing of contaminated wastes, which includes a cylindrical housing 101, having a lower side wall portion 102 and an upper side wall portion 104. The lower cylindrical side wall portion 102 comprises an inwardly turned circular seat 105 with a bottom wall or "plug" 106 positioned inside the lower cylindrical side wall portion 102. The bottom wall 106 is supported on the circular seat 105. The upper side wall portion 104 of the cylindrical housing 101 includes an opening 109 (FIG. 11) leading to a holding chamber 108 for collecting contaminated wastes.

A telescoping member 110 comprises a cylindrical side wall 111 which is of sufficient internal breadth to telescopically fit about the lower side wall portion 102, as well as the upper side wall portion 104. The cylindrical side wall 111 comprises an inwardly turned circular seat 112 which supports an end wall 115.

An absorbent material, preferably an absorptive pack 120, is placed in the holding chamber 108 and rests on bottom wall 106 where it is most likely to come in contact with liquids emitted from the wastes.

As seen in FIG. 11, the telescoping member 110 is formed to telescope about the lower side wall portion 102 when the opening 109 is temporarily exposed to collect contaminated wastes 121. The telescoping member 110 thereby provides a stabilizing base for the system 100 as contaminated wastes are being collected in the collector. In a hospital environment, this larger configuration may be advantageously employed as a "kick bucket" for receiving large volumes of medical wastes, such as surgical masks, drapes, garments, or kit packs in an operating or an emergency room.

FIG. 12 illustrates the telescoping member 110 mounted about the upper side wall portion 104 of the system 100. When the telescoping member 110 telescopes about the upper said wall 104, the opening 109 is thereby sealed. Thus, as shown in FIG. 12, the telescoping member 110 provides a cover for the opening 109 of the system so as to provide a secure container for contaminated wastes, especially when the wastes must be handled and transported from one location to another.

The preferred material of construction in all of the above embodiments comprises biodegradable, or otherwise known as non petroleum-based materials selected from the following group: natural cellulosic-based materials such as wood, cardboard, particle board and fiber board, non-natural cellulosic materials, such as rayon, cellophane, and cellulose-nitrate, and other materials, such as natural rubber and natural wax which when burned emit no more than trace amounts of sulphur or chlorine. These materials add to the Btu loading for completely rendering and transforming the contents of the collectors. Additional qualities which can be taken singly or in combination, are absorbent for absorbing liquids emitted from the medical wastes, leak resistant so as to avoid leaking liquid wastes, puncture resistant so as to avoid a needle of a syringe puncturing the wall of the collector from inside the holding chamber, and rigid so as to be self supportive and avoid inadvertent crushing.

Figure 13:
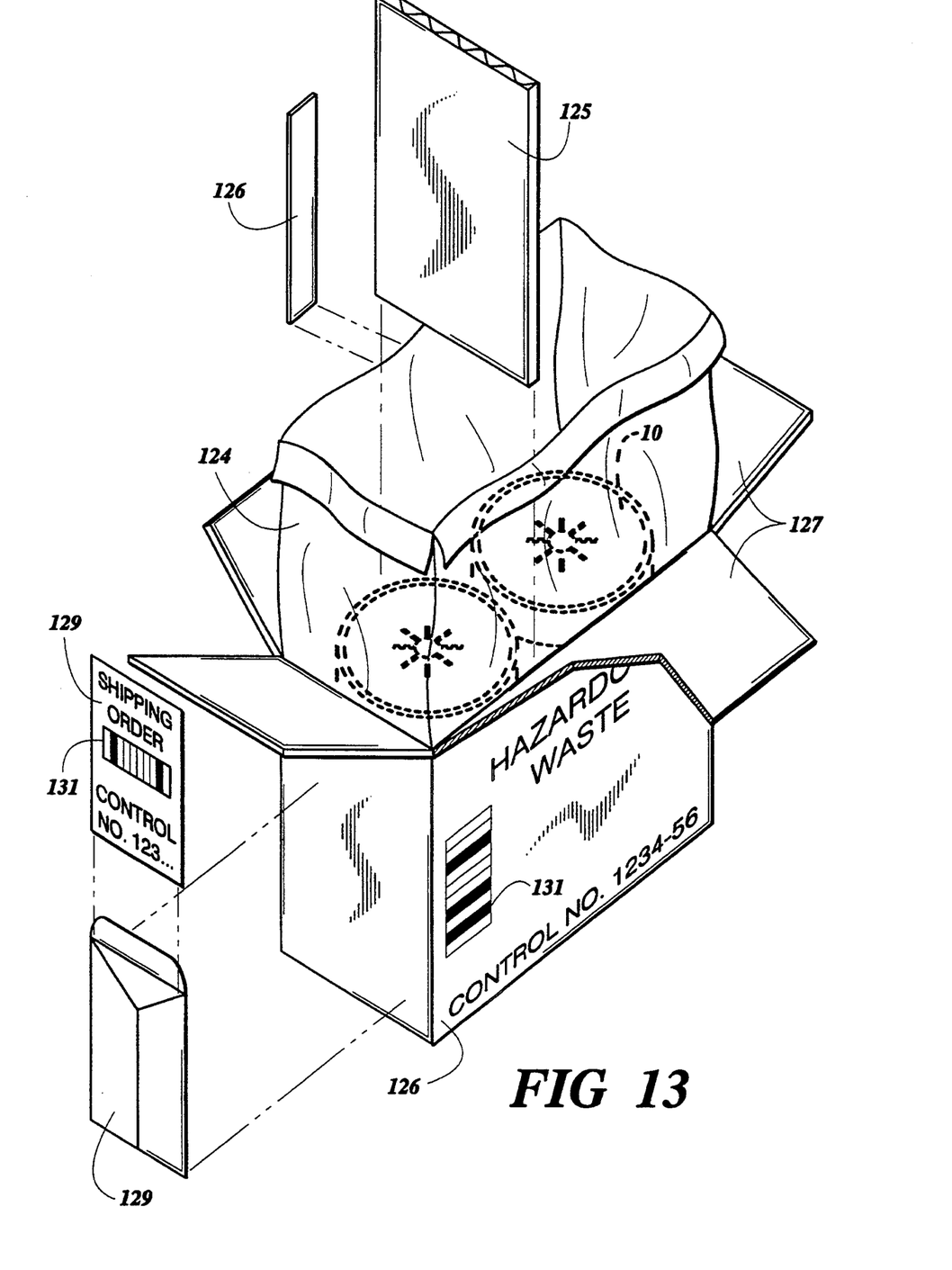
FIG. 13 is a perspective view of the housings which contain the medical wastes placed in a larger container for shipment to the site of an incinerator or other destruction facility.
Figure 14:
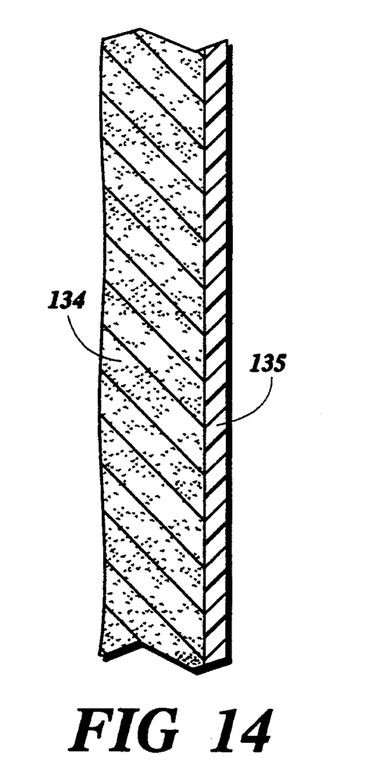
FIG. 14 is a cross section of a portion of the bag of FIG. 13.

FIG. 13 discloses a system for transporting the medical wastes from the collection site to the destruction site, usually an incinerator. Several of the collectors, such as two of the collectors 10 of FIG. 1, are placed in a leak proof red or yellow bag 124 with a corrugated cardboard divider 125 placed therebetween. The divider 125 functions as a shock absorber between the collectors 10. As illustrated in FIG. 14, a preferred embodiment of the bag 124 is sealed around the collectors 10, and the bag 124 and its contents are placed in an outer box 126. An adhesive strip 126 or a wire twist tie is provided for maintaining the top of the bag closed. The flaps 127 of the box are folded closed over the bag 124. Bag 124 may be made of laminated sheet material such as plastic and super absorber such as sodium acrylate, which is a common laminated material used for diapers for infants. As illustrated in FIG. 14, the inside layer 134 of the bag is the super absorbent material such as sodium acrylate and the outside layer 135 is the liquid impermeable plastic layer. The liquid impermeable layer assures that any liquid emitted from the wastes in the collector will not escape from the package. The absorbent layer accomplishes two functions: liquid absorption, and shock absorption. Should liquid emanate from the collector, the liquid absorption material will absorb and contain the liquid. Further, the layer 134 is compressible and therefore functions as a shock absorber in the event that the outer, secondary container and its contents are dropped, tossed or otherwise jarred in handling.

The individual collectors 10 as well as the box 126 are clearly marked as containing hazardous wastes, and are further marked with a control number and a bar code 131.

A shipping order 128 is received in a transparent envelope 129, with the envelope being adhesively attached to the box 126. The shipping order directs the box and its contents to the proper destination. The shipping order will be filled in with the identifying indicia of each of the collectors 10, so as to provide external identification of the collectors and their contents.

Upon arrival of the box 126 and its contents at the incinerator site, the shipping order is removed and recorded, and the entire box 126 is cast unopened into the incinerator and burned. The shipping order identifies the contents or class of waste material in the box 126, so that care can be taken by the incineration facility to properly destroy the box and its contents. Preferably, the shipping order is used by the incinerator facility to provide return information to the sender, which verifies to the sender that the box and its contents have been received and destroyed at the incineration site.

Preferably, the box 126 is fabricated of combustible materials, such as cellulose, of the type which emits only trace amounts of chlorine, sulphur or other atmospheric pollutants when burned, and which degenerates into substantially only biodegradable ash.

If the collectors 10 are to be delivered through the U.S. Postal Service from the collection site to the incineration site, the regulations of the domestic mail services will be followed, particularly §124, DMMIssue 45, dated Dec. 20, 1992.

In some of the above described embodiments, the mass of the material used to form the housing is matched with the volume of the holding chamber which will receive a predetermined mass of syringes and other anticipated typical medical wastes so that the amount of the material of the housing is sufficient to emit enough heat when burned to transform the medical wastes in the holding chamber into a substantially noncontaminated and noncombustible residue or ash. After incineration of the collector housing, the ash of the collector itself will consist of a biodegradable "mineral" ash.

Figure 15:
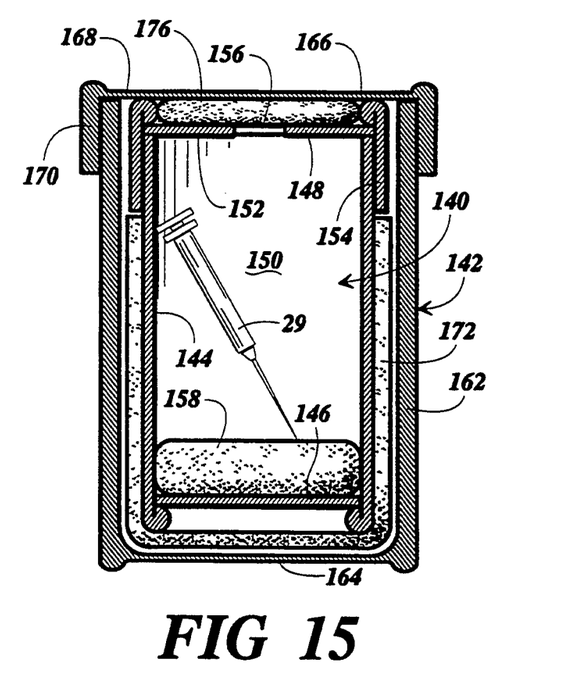
FIG. 15 is a side cross-sectional view of another embodiment of a double wall collector.

As illustrated in FIG. 15, another embodiment of the collector system includes a inner, primary housing 140, and an outer, secondary shipping container 142. The inner primary container includes the cylindrical side wall 144, flat bottom wall 146, and lid 148, all of which define the holding chamber 150. The lid includes the top wall 152 and the rim structure 154 that telescopes downwardly about the upper end portion of the cylindrical primary container 140. Opening 156 is formed in the top wall 148 for the receipt of used hypodermic needle syringes 29. An absorbent pack is placed in the holding chamber 150, resting against bottom wall 146. Although gravity usually holds the absorbent pack in its position illustrated in FIG. 15 where it rests upon the bottom wall 146, adhesive can be applied between the facing surfaces of the absorbent pack and the bottom wall to assure that the absorbent pack is retained in its flat, abutting position with respect to the bottom wall, and with its perimeter juxtaposed the inside facing surfaces of the cylindrical side wall 144 of the primary container.

The secondary shipping container 142 includes a cylindrical side wall 162, bottom wall 164 and lid assembly 166. The lid assembly includes the top wall 168 and rim 170 which telescopes downwardly about the upper end portion of cylindrical side wall 162. If desired, spiral threads can be formed between the facing surfaces of the lid 166 and the cylindrical side wall 162.

An absorbent package shaped like a sock 172 is positioned between the inner primary container 140 and the outer shipping container 142, with the sock surrounding the lower portion of the inner container 140 and extending upwardly thereabout. The sock contains liquid absorbent material such as sodium acrylate, which is also shock absorbent material. Should any liquid be emitted from the lower portion of the primary container 140, it will contact the liquid absorbent sock 172 and therefore be absorbed by the material of the sock.

A disc-shaped absorbent pad 176 is placed on top of the lid 148 of the inner primary container 140, so that the pad 176 covers the opening 156 and fits in the space between lid 148 of the primary container and lid 166 of the secondary shipping container. Typically, the thickness of the pad 176 is slightly greater that the anticipated space between the lids 148 and 166, so that when the external lid 166 is applied to the package, the pad 176 will be slightly compressed into positive contact with the top wall 152 of the lid 148. This assures that the opening 156 will be closed, and any liquid from the holding chamber 150 that attempts to pass through the opening 156 will be contacted by and absorbed by the pad 176. Further, the diameter of the pad 176 is large enough to substantially fill the inner space formed by the rim 154 of the lid 168, so that if liquid should seep about the perimetal edge of the top wall 148, it will be contacted by and absorbed by the pad 176.

In the embodiment illustrated, the absorbent sock 172 has been applied to the inner, primary collector container 140; however, it will be understood that the sock 172 could be formed of slightly larger dimensions so as to contact the interior surfaces of the outer shipping container 142.

The inner, primary container 140 of FIG. 15 is formed of rigid, combustible, liquid impermeable material, preferably a biodegradable material. Likewise, the outer shipping container 142 is formed of rigid, combustible, self-supportive, liquid impervious material; however, if desired for strength during shipping, the outer shipping container can be formed of plastics for the cylindrical side wall and bottom wall, and the lid and possibly the bottom wall can be formed of metal, as may be desired by the manufacturer.

The dual wall structure and the liquid absorbent and shock absorbent sock 172 of FIG. 15 assure that the collector will be virtually indestructible and leak-proof during normal shipping functions, substantially without hazard of puncture, crushing or other destruction which would cause the contents of the collector to be leaked from or discharged from the collector.

In some of the above described embodiments, geometric variations such as wall thickness and mass of the housing and the insert, can be adjusted relative to the internal collection volume of the holding chamber, to yield a predetermined ratio of the ash of the housing with respect to the ash of the medical waste, when incinerated. This ratio can be adjusted by increasing or decreasing the thickness of the collector walls so as to increase or decrease the mass of the collector, or by changing the size and/or shape of the collector without changing the weight of the collector.

Therefore, if it is desired that the ashes of incineration of the collector and its contents include more paper ash, which is biodegradable, and less plastic ash, which is not biodegradable, the manufacturer of the collector can adjust the size, volume and/or mass of the collector. Thus, the ash content of the collector and its contents can be adjusted so that the ash can be used, for example, as a fertilizer if it contains a high ratio of paper ash, or as an additive to a building material such as concrete or tar if it contains a high ratio of plastic ash.

EXAMPLE

For example when the empty collector is 250 mm high and 100 mm in inside diameter, the available volume is calculated: $h\pi r^2 = 1,963,494$ mm$^3$. If the syringe is 10 mm in outside diameter and 100 mm long, the occupied volume is calculated: $l\pi^2 = 7,854$ mm$^3$. At 100% packing (theoretical case), 250 syringes fit into the collector's "occupied volume". For a practical case, the packing density is estimated at 25% of the theoretical full packing condition, which is 62 syringes. If each syringe weighs 0.75 ounces, there are 21.33 syringes per pound, so the loaded collector holds 2.93 pounds of syringes. If the empty collector comprises 8 ounces of cardboard, which yields 10% ash by weight, then upon burning the collector, the anticipated burn results of the collector are 0.05 pounds of ash. Assuming the syringes are plastic and yield 1.7% ash by weight, then upon burning, the anticipated burn results of 2.93 pounds of syringes yield 0.05 pounds of ash. Thus, upon burning the collector filled with a practical load of syringes the resulting ratio of plastic ash to paper ash is 1 to 1.

The wall thickness and other geometric variations of the collector housing can be tailored to accommodate the needs of different applications, and to accommodate different items to be deposited in the collectors and can be adapted relative to the collection volume within the housing to further control leak-resistance, puncture-resistance, incinerability, biodegradability, and other factors related to the system for collecting and disposing of medical wastes.

The absorbent pack 30 (FIG. 2) preferably is of a mass to absorb more liquid than can be contained in the holding chamber of the collector. Further, the absorbent material can be placed directly in the holding chamber (FIG. 2) or in an adjacent chamber (FIG. 4) or in both the holding chamber and an adjacent chamber (FIG. 9).

Although this invention has been described in relation to hypodermic needle syringes and other medical wastes, it can be used with other types of wastes, particularly any types of contaminated wastes that should be carefully disposed of by burning.

While this invention has been described in relation to these preferred embodiments, it will be apparent to those skilled in the art that the invention is susceptible to additional embodiments without departing from the spirit and scope of the invention. Therefore, it is intended that the invention not be limited except by the claims.

We claim:

1. A disposable combustible collector for receiving and incinerating used hypodermic needle syringes and other contaminated medical wastes comprising:

a housing having a sidewall structure and end walls and defining a holding chamber with an opening in an end wall in communication with said holding chamber for the receipt of hypodermic needle syringes;

at least said side wall structure of said housing being formed of liquid leak resistant, hypodermic needle puncture resistant, combustible material;

a liquid absorption pack fabricated of liquid absorbent material contained in said housing for absorbing liquid emitted from the syringes placed in said housing;

said absorption pack being of a size greater than the effective breadth of said opening so that the absorption pack cannot pass through said opening; and the side walls of said housing including indicia which identify the housing as containing used hypodermic needle syringes;

whereby when the housing is placed in and upright attitude with the opening of the end wall facing upwardly, the liquid absorption pack rests on the lower end wall and used hypodermic needle syringes are moved through the opening and downwardly into the holding chamber, and liquids emitted from the syringes and which contact the liquid absorption pack are absorbed by the absorbent material and not leaked from the housing, and the housing and its contents are burned without opening the housing and the material of the collector burns and aids in the incineration of the syringes.

2. The disposable collector of claim 1 and wherein said side wall structure of said housing is formed of a group of materials selected from: natural cellulosic materials consisting of fiberboard, cardboard, molded cellulose, paper stock, wood and particle board, and non-natural cellulosic materials consisting of rayon, cellophane, and cellulose-nitrate, which are combustible and biodegradable, and when burned evolve no more than trace levels of chlorine or sulphur and yield substantially only biodegradable ash.

3. A disposable burnable collector for receiving and incinerating used hypodermic needle syringes and other forms of medical wastes comprising:

a housing defining a holding chamber and defining an opening in communication with said holding chamber for the receipt of wastes, said housing comprising an inner primary container defining said holding chamber and an outer shipping container surrounding said inner primary container, said primary and shipping containers formed of liquid leak resistant and hypodermic needle puncture resistant burnable materials, liquid absorbent material positioned in said holding chamber in contact with the bottom of said holding chamber for absorbing liquid emitted from said wastes placed in said housing;

whereby when wastes are placed in the holding chamber liquid emitted from the wastes and which contacts the absorbent material is absorbed by the absorbent material, and the collector and its contents are incinerated without opening the housing and the material of the housing burns.

4. The disposable collector of claim 3 and further including liquid absorbent material substantially surrounding said inner primary container.

5. The disposable collector or claim 4 and wherein said liquid absorbent material comprises a bag formed of laminated sheet material having an inner layer of liquid absorbent material facing and surrounding said inner primary container, and an outer layer of liquid impermeable material facing said outer shipping container.

6. The disposable collector of claim 5 and wherein said liquid absorbent material is formed of compressible material and is of a thickness to function as a shock absorber between said inner primary .container and said outer shipping container.

7. The disposable collector of claim 4 and wherein said liquid absorbent material comprises a sock surrounding at least a portion of said inner primary container.

8. The disposable collector of claim 4 and further including a liquid absorbent pad positioned in abutment with said opening for absorbing liquids passing through said opening.

9. The disposable collector of claim 3 and wherein said liquid absorbent material comprises a self supporting liquid absorption pack of a size and shape effectively larger than said opening so that the liquid absorption pack cannot pass through said opening.

10. The disposable collector of claim 3 and wherein said insert is formed essentially of sodium acrylate.

11. A process of collecting and incinerating used hypodermic needle syringes and other medical wastes comprising:
providing a housing formed of a combustible, hypodermic needle puncture resistant and liquid leak resistant material which defines a holding chamber sized and shaped to receive and contain hypodermic needle syringes;
placing indicia On said housing which identifies the contents of the housing and the incineration destination to which the housing is to be delivered;
placing an absorption pack formed of liquid absorbent material in the holding chamber;
placing used hypodermic needle syringes in the holding chamber;
absorbing liquid emitted from the syringes with the absorbent material of the absorption pack;
delivering the housing and its contained syringes to the incineration destination; and
incinerating the housing and its .contents in the incinerator at the incineration destination in accordance with the contents identified On the housing without removing the syringes from the holding chamber of the housing.

12. The process of claim 11 and wherein the step of placing an absorption pack in the holding chamber comprises placing an absorption pack of a size sufficient to absorb all of the liquid emitted from the syringes in the holding chamber.

13. The process of claim 11 and wherein the step of providing a housing of a combustible material comprises providing a housing that defines a holding chamber of a size and shape which receives up to a predetermined number of hypodermic needle syringes, and the housing being formed of at least a sufficient amount of combustible material to destroy by burning at least the predetermined number of syringes, and wherein the step of incinerating the housing and its contents comprises aiding in the burning of the syringes by the burning of the housing.

14. A disposable collector for receiving and incinerating at an incineration destination of medical wastes, including used hypodermic needle syringes needing incineration comprising:
a housing defining a holding chamber and an opening in the upper portion of-said housing in communication with said holding chamber from outside said housing for the receipt of hypodermic needle syringes through said opening into said holding chamber, said housing being formed of materials that are combustible in a furnace environment and which are self supportive for retaining the shape of the housing during its intended use prior to incineration;
indicia on said housing which identifies the contents of said housing and the incineration destination to which said housing is to be delivered;
liquid absorptive material positioned in the lower portion of said housing for absorbing liquid emitted from the medical wastes placed in said holding chamber;
means for retaining the hypodermic needles in said holding chamber;
so that when liquid-bearing medical wastes are inserted through the opening and into said holding chamber, liquid emitted from the medical wastes and which liquid contacts the liquid absorption pack in the lower portion of said housing tends to become absorbed by the liquid absorptive material of the absorption pack and is retained in the absorption pack and does .not leak from the housing prior to the housing being burned and the housing and its contents are delivered to and burned in an incinerator at the incineration destination without opening the housing.

15. The disposable collector of claim 14 and wherein said housing comprises an inner primary container which defines said holding chamber and an outer shipping container which surrounds said primary container.

16. The disposable collector of claim 15 and wherein said absorptive material comprises an absorption pack is positioned in said holding chamber.

17. The disposable collector of claim 15 and wherein said absorptive material is positioned in said housing outside said holding chamber.

18. The disposable collector of claim 15 and wherein said absorptive material comprises an absorption pack positioned between said primary container and said shipping container.

19. The disposable collector of claim 14 and wherein said collector is fabricated of combustible biodegradable materials which, when burned, aid in the incineration of the medical wastes contained in said holding chamber.

20. The disposable collector of claim 14 and wherein said housing is sufficiently liquid leak resistant so as to safely contain the medical wastes, including liquid carried by the medical wastes and emitted from the medical wastes in the holding chamber.

21. The disposable collector of claim 14 and wherein said housing is sufficiently puncture-resistant to accommodate and to resist penetration by hypodermic needles from inside said housing.

22. The collector of claim 14 and wherein said housing is substantially cylindrical with a cylindrical side wall and substantially flat end walls, and wherein said opening is formed in a first one of said end walls and is of a breadth adequate to receive therethrough hypodermic needle syringes, and wherein said liquid absorption means comprises an absorption pack resting on the end wall opposite to said first end wall when said opening faces upwardly.

23. The collector of claim 14 and wherein said housing comprises dual sidewalls, including an inner sidewall and an outer sidewall, said inner side wall being shorter than said outer side wall, and the ends of said inner side wall being offset inwardly of the ends of said outer sidewall.

24. A disposable collector for receiving and incinerating at a remote incinerator of medical wastes including used hypodermic needle syringes needing incineration comprising:

a housing defining a holding chamber, an opening in said housing in communication with said holding chamber from outside said housing for the receipt therethrough of medical wastes in said holding chamber;

said housing comprising a double wall structure surrounding said holding chamber with an inner wall structure and an outer wall structure surrounding said inner wall structure, with said holding chamber defined by said inner wall structure;

indicia carried by said housing for identifying the contents of said housing and the incineration destination to which said housing and its contents are to be delivered;

liquid absorbent material positioned in said collector for absorbing liquid emitted from the medical wastes in said holding chamber and which liquid contacts the absorbent material;

said opening including means for retaining the medical wastes in said holding chamber;

whereby the medical wastes are inserted through the opening into the holding chamber of the inner wall structure and the double wall structure of the housing and its contents are delivered to an incinerator at the incineration destination where the housing and its contents are incinerated without removing the contents from the housing.

25. The disposable collector of claim 24 and wherein the double wall structure comprises two cylindrical side walls, one fitted inside the other and fabricated of combustible, puncture resistant and leak resistant materials.

26. The disposable collector of claim 24 and wherein the double wall structure comprises the inner wall structure fitted inside the outer wall structure.

27. The disposable collector of claim 24 and wherein said collector defines a second chamber adjacent said holding chamber, and wherein at least some of said absorbent material is contained in said second chamber, and wherein liquid emitted from the medical wastes in said holding chamber and into said second chamber and which liquid comes into contact with the absorbent material tends to become absorbed by the absorbent material.

28. A method of collecting and incinerating medical wastes including used hypodermic needle syringes needing incineration, comprising:

providing a hypodermic needle puncture resistant, liquid leak resistant housing fabricated at least in part of combustible material and defining a holding chamber for receiving and retaining medical wastes;

applying indicia to said housing for identifying the contents of said housing and the incinerating destination of said housing;

placing liquid absorbative material in the housing;

placing used syringes in the holding chamber of the housing;

absorbing with the absorptive material in the housing the liquid emitted from the used syringes and which liquid contacts the absorptive material;

moving the housing and its contents to an incinerator at the incineration destination;

placing the housing and its contents in an incinerator without opening the housing; and burning the housing and its contents in the incinerator in accordance with the indicia applied to the housing.

29. The method of claim 28 and wherein the step of placing the liquid absorbent material in the housing comprises placing the absorbent material in a second chamber of the housing separate from the holding chamber, and wherein the step of absorbing with an absorptive material in the housing the liquid emitted from the medical wastes comprises absorbing in the second chamber the liquid leaked from the holding chamber into the second chamber.

30. The method of claim 28 and wherein the step of providing a housing comprises providing a cylindrical housing having inner and outer cylindrical sidewalls fabricated of combustible material and an opening defined by the housing for receiving the used syringes.

31. The method of claim 28 and wherein the step of placing liquid absorbent material in the housing comprises placing an absorption pack in the housing of a size larger than the effective breadth of the opening to retard movement of the absorption pack out of said housing.

32. A disposable combustible collector for receiving and incinerating used hypodermic needle syringes and other contaminated medical wastes comprising:

a primary container defining a holding chamber for containing the syringes;

a flexible bag sized and shaped to receive and enclose said primary container, said bag comprising leak resistant liquid absorbent material;

a shipping container sized and shaped to receive and enclose said primary container and said bag in which said primary container is received;

indicia applied to said shipping container for identifying the contents of said shipping container and an incinerating destination of said collector and its contents;

whereby used syringes are deposited in the holding chamber of the primary container, the primary container enclosed in the bag, and the primary container and its bag enclosed in the shipping container and transported to the incineration destination and incinerated without opening the shipping container in accordance with the indicia applied to the shipping container; and liquid emitted from said primary container is absorbed by and not leaked from the bag prior to the collector being incinerated.

33. The collector of claim 32 and wherein said flexible bag is formed of sheet material having an inner layer of liquid absorbent material for facing said primary container and an outer layer of liquid impermeable material for facing said shipping container.

34. The collector of claim 32 and wherein said inner and outer layers of said bag sheet material are formed of combustible materials that burn in an incinerator.

* * * * *